United States Patent
Puig et al.

(10) Patent No.: US 10,342,441 B2
(45) Date of Patent: Jul. 9, 2019

(54) ESTIMATING HEART RATE BY TRACKING OPTICAL SIGNAL FREQUENCY COMPONENTS

(71) Applicant: QUALCOMM Incorporated, San Diego, CA (US)

(72) Inventors: Carlos Puig, Santa Clara, CA (US); Ramin Samadani, Menlo Park, CA (US); Russel Martin, Menlo Park, CA (US)

(73) Assignee: QUALCOMM Incorporated, San Diego, CA (US)

( * ) Notice: Subject to any disclaimer, the term of this patent is extended or adjusted under 35 U.S.C. 154(b) by 76 days.

(21) Appl. No.: 15/012,673

(22) Filed: Feb. 1, 2016

(65) Prior Publication Data

US 2016/0249820 A1    Sep. 1, 2016

Related U.S. Application Data

(60) Provisional application No. 62/126,288, filed on Feb. 27, 2015.

(51) Int. Cl.
*A61B 5/02* (2006.01)
*A61B 5/024* (2006.01)
*A61B 5/00* (2006.01)

(52) U.S. Cl.
CPC ...... *A61B 5/02416* (2013.01); *A61B 5/02438* (2013.01); *A61B 5/681* (2013.01); *A61B 5/721* (2013.01); *A61B 5/7257* (2013.01); *A61B 2562/0219* (2013.01)

(58) Field of Classification Search
CPC ........ A61B 2562/0219; A61B 5/02416; A61B 5/02438; A61B 5/681; A61B 5/721; A61B 5/7257

See application file for complete search history.

(56) References Cited

U.S. PATENT DOCUMENTS

| | | | |
|---|---|---|---|
| 6,868,381 B1 | 3/2005 | Peters et al. | |
| 7,020,507 B2 | 3/2006 | Scharf et al. | |
| 8,920,332 B2 | 12/2014 | Hong et al. | |
| 2004/0039420 A1* | 2/2004 | Jayne | A61B 5/1107 607/5 |

(Continued)

FOREIGN PATENT DOCUMENTS

| | | |
|---|---|---|
| WO | 2004075746 A2 | 9/2004 |
| WO | 2004080300 A1 | 9/2004 |
| WO | 2008055173 A2 | 5/2008 |

OTHER PUBLICATIONS

International Search Report and Written Opinion—PCT/US2016/016207—ISA/EPO—dated Apr. 22, 2016.

*Primary Examiner* — Mark D Remaly
(74) *Attorney, Agent, or Firm* — Kilpatrick Townsend & Stockton

(57) ABSTRACT

Methods, systems, computer-readable media, and apparatuses for estimating a user's heart rate using a PG signal are presented. In some implementations, the heart rate is estimated by computing a frequency-domain PG, identifying one or more features in the frequency-domain PG, selecting qualified features from the one or more features, and constructing one or more traces. In some implementations, an accelerometer signal can be used for motion cancellation to eliminate traces that are motion artifacts.

28 Claims, 11 Drawing Sheets

(56) References Cited

U.S. PATENT DOCUMENTS

| | | |
|---|---|---|
| 2007/0213619 A1 | 9/2007 | Linder et al. |
| 2009/0119762 A1 | 5/2009 | Thomson et al. |
| 2010/0113948 A1 | 5/2010 | Yang et al. |
| 2011/0066041 A1 | 3/2011 | Pandia et al. |
| 2012/0130263 A1* | 5/2012 | Pretorius .............. A61B 5/0452 600/509 |
| 2012/0190124 A1 | 7/2012 | Smith et al. |
| 2014/0213858 A1 | 7/2014 | Presura et al. |
| 2014/0213863 A1 | 7/2014 | Loseu et al. |
| 2014/0275854 A1 | 9/2014 | Venkatraman et al. |

* cited by examiner

ESTIMATING HEART RATE BY TRACKING OPTICAL SIGNAL FREQUENCY COMPONENTS

CROSS-REFERENCE TO RELATED APPLICATIONS

This application claims the benefit of U.S. Provisional Application No. 62/126,288, entitled "HEART RATE ESTIMATION," filed on Feb. 27, 2015, which is hereby incorporated herein by reference, in its entirety.

FIELD

Aspects of the disclosure generally relate to systems and methods of determining heart rate using signals.

BACKGROUND

A user's heart rate can be leveraged as an input to various health and fitness endeavors. It can be used to estimate energy expenditure, set exercise targets, determine stress, and estimate level of fitness. Several devices, among them wearable or portable devices, are used to determine a user's heart rate using optical signals. Some wearable devices incorporate optical heart rate monitors which do not require a chest strap. These wearable devices can provide a quick and easy method of estimating a user's heart rate under various conditions.

There may be interest in determining heart rate in various modes. For example, heart rate may be determined continuously, such as during exercise; heart rate may be determined in the background throughout a period of time or continually when the wearable device is on; and heart rate may be determined in response to a specific one-time user request.

In one example, heart rate may be estimated from the optical signal measured by a sensor such as a pulse oximeter using a technique called photoplethysmography (PPG). In other examples, a combination of LED and photodiode can be used in place of or in addition to a pulse oximeter. Heart rate estimates through most methods can be subject to noise from various sources. For example, motion severely degrades the quality of the optical signal resulting in inaccurate heart rate estimates when a user is not substantially still.

BRIEF SUMMARY

Herein, some implementations of systems and methods are described for estimating a heart rate of a user. Such a method may include obtaining a plethysmogram (PG) signal. In some implementations, the PG signal may be obtained from a sensor attached to or in the proximity of a wearable or mobile electronic device. In one example, the sensor can be a pulse oximeter. The method may also include computing a frequency-domain PG based on the obtained PG signal. Additionally, the method may include identifying one or more features from the frequency-domain PG, applying at least one criterion to select a qualified feature from the one or more features, and constructing one or more traces in a frequency-versus-time mapping using the qualified feature. The qualified feature may represent a position in the frequency-versus-time mapping. In other words, a qualified feature may represent a set of a timestamp and a frequency value. A PG trace may comprise a group of such related positions corresponding to qualified features. The method may further include selecting a PG trace from the one or more PG traces as representative of the heart rate for a given period of time. The selected PG trace may be used to estimate the heart rate of the user.

In one example, the one or more features could correspond to one or more peaks in the frequency-domain PG. Other features from the frequency-domain PG such as widths, areas, and other graphical features can be used in other examples.

In some implementations, computing the frequency-domain PG signal based on the obtained PG signal may comprise applying a Fast Fourier Transform to the obtained PG signal. In some implementations, the frequency domain PG signal may comprise a power spectrum of the PG signal. In implementations, computing the frequency-domain PG signal may comprise applying various types of Fourier transforms such as Discrete Time Fourier Transform.

In some implementations, the system and method of estimating the heart rate may include calculating a frequency-domain accelerometer (ACL) signal based on an obtained ACL signal. The ACL signal may be obtained from a sensor such as an accelerometer located on or proximate to a wearable or mobile electronic device. The method may include identifying one or more ACL features from the frequency-domain ACL signal, selecting qualified ACL features from the one or more ACL features from the frequency-domain ACL signal, and constructing ACL traces in the frequency versus time mapping using the qualified ACL features. Each qualified ACL feature may represent an ACL position in the frequency-versus-time mapping. An ACL trace may comprise a group of related ACL positions. The method may additionally include determining whether to eliminate one or more PG traces based at least in part on the ACL traces. In some implementations, ACL traces may be used to distinguish physical movement and motion artifacts from the heart rate. In some implementations, upon determining that one or more PG traces should be eliminated, one or more PG traces may be eliminated. The heart rate may then be estimated based on the remaining PG traces.

In some implementations, determining whether to eliminate one or more PG traces may comprise eliminating PG traces if an inter-trace distance between an ACL trace and a PG trace is lesser than a threshold distance.

In some implementations, the system and method may include maintaining a set of active traces. Such maintaining of a set of active traces may comprise removing from the set of active traces any trace with a trace age older than a maximum age. The trace age can be the difference between a current timestamp and a previous timestamp in a trace.

In some implementations, constructing one or more traces may comprise adding a qualified feature to any trace whose most recent frequency differs from the qualified feature's frequency by less than a threshold difference. In some implementations, a new trace may be constructed if the qualified feature's frequency is different from the most recent frequency of the trace by more than a threshold amount.

According to some aspects, the at least one criterion to select a qualified feature from the one or more features may include a magnitude and a width of a peak region. The peak region may refer to an area surrounding a peak identifiable by certain characteristics.

In some implementations, the system and method may further comprise estimating a quality metric for the heart rate. The quality metric may indicate a reliability or accuracy value for the estimated heart rate.

In some implementations, the system and method may further comprise modifying the estimated heart rate based on prior information. For example, in some implementations, such prior information may comprise known probabilities of pairs of accelerometer power and heart rate for a specific demographic of population.

In some implementations, the heart rate may be estimated at a given time for a requested time. In some implementations, the requested time may be earlier than the given time. In some implementations, estimating the heart rate for a requested time may comprise back-tracking through a heart rate trace to the requested time.

BRIEF DESCRIPTION OF THE DRAWINGS

Aspects of the disclosure are illustrated by way of example. In the accompanying figures, like reference numbers indicate similar elements, and.

DETAILED DESCRIPTION

Figure 1:
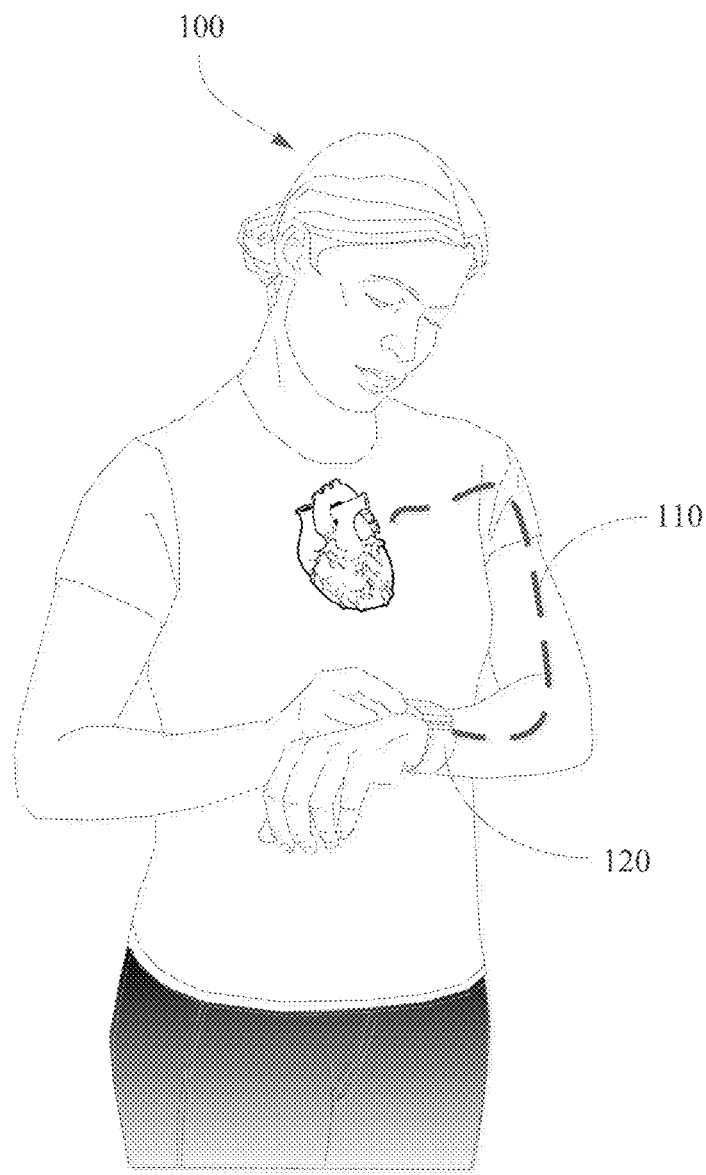
FIG. 1 illustrates a simplified diagram of a user monitoring her heart rate using implementations.

Certain aspects and implementations of this disclosure are provided below. Some of these aspects and implementations may be applied independently and some of them may be applied in combination as would be apparent to those of skill in the art. In the following description, for the purposes of explanation, specific details are set forth in order to provide a thorough understanding of implementations of the invention. However, it will be apparent that various implementations may be practiced without these specific details. The figures and description are not intended to be restrictive.

The ensuing description provides exemplary implementations only, and is not intended to limit the scope, applicability, or configuration of the disclosure. Rather, the ensuing description of the exemplary implementations will provide those skilled in the art with an enabling description for implementing an exemplary implementation. It should be understood that various changes may be made in the function and arrangement of elements without departing from the spirit and scope of the invention as set forth in the appended claims.

Specific details are given in the following description to provide a thorough understanding of the implementations. However, it will be understood by one of ordinary skill in the art that the implementations may be practiced without these specific details. For example, circuits, systems, networks, processes, and other components may be shown as components in block diagram form in order not to obscure the implementations in unnecessary detail. In other instances, well-known circuits, processes, algorithms, structures, and techniques may be shown without unnecessary detail in order to avoid obscuring the implementations.

Also, it is noted that individual implementations may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

Furthermore, implementations may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable medium. A processor(s) may perform the necessary tasks.

A user may request a heart rate estimate from a mobile or wearable device in at least three scenarios: (1) continuously during a period of exercise when the user monitors the rate closely; (2) unobtrusively in the background to review later and compute summary statistics; (3) as a one-time request at a time of interest.

FIG. 1 is an illustration of a user 100 monitoring her heart rate, for example following activity, using wearable device 120 according to an implementation. User 100's heart rate is reflected in her blood flow, or pulse, and communicated to an area of her body in proximity to wearable device 120 through blood-vessels such as blood-vessel 110.

Wearable device 120 can estimate the heart rate of a user using, for example, optical signals. In such methods, light is emitted from an LED in a sensor in wearable device 120 that is in close proximity to the user's skin, such as on the user's wrist in FIG. 1. In other examples, the sensor can be in proximity to a user's finger or other area. The light is scattered (or partially reflected) upon entry into the user's body. The scattered light is detected by a photo-sensor or photodiode in the sensor, which measures the intensity of the scattered light. In implementations, the sensor can be a pulse oximeter that can be based on oxygen absorbance measurements.

Some of the light can be scattered by physical objects between the sensor and the user's skin; some of the light can be scattered by the surface of the user's skin; and some of the light can be scattered by layers just underneath the surface of the user's skin comprising blood vessels. The light scattered by the layers that have blood flow may be the most significant for heart rate measurement because the properties of such layers change with the pulse of the user. Hence, the properties of the scattered light from these layers include properties indicative of the pulse or heart rate of the user.

However, the scattered light can be heavily affected by the user's movement. For example, if the user is flexing her fingers, even mild muscle contractions and tendon movements can be sufficient to affect the scattered light. In order to accurately estimate the heart rate of the user, such artefacts of motion and other noise may need to be filtered from the scattered light. Properties of the scattered light can also vary from person to person based on several characteristics such as skin color. Consequently, the scattered light that forms the input signal to the sensor for heart rate estimation can include noise that is not representative of the user's heart rate.

In general, poor signal-to-noise ratio can result from, at least: low-quality heart rate signal from some individuals due to their physiology (dark skin, light skin, tattoos, hair, vascularization of the wrist), poor mechanical coupling between the sensor and the user's skin (how close the sensor can be to the skin), movements in the users internal tissues from muscle contractions, or higher levels of motion from the user's activities or vehicle (such as when a user is in a car or a bicycle). Heart rate is typically reported in Beats Per Minute (BPM), which can be converted to Hertz (Hz) by dividing by 60. The frequency of a signal can be expressed, for example, in BPM.

Although explained in the specification with reference to scattered light (photoplethysmogram or PPG), the same or similar techniques can be used with other optical or non-optical signals. For example, different kinds of plethysmogram (PG) (measuring the volume of a body part) signals such as photoplethysmogram (PPG) or inductance plethysmogram can be used as the input signal for described methods and devices.

In some examples, wearable device 120 can also include an accelerometer. The accelerometer can detect and measure acceleration of wearable device 120 and provide an accelerometer input to wearable device 120. The accelerometer can be used to measure acceleration of wearable device 120. In implementations, the accelerometer may include a single-axis or a multi-axis accelerometer, and can be used to detect a magnitude and a direction of the measured acceleration as a vector quantity.

Figure 2:
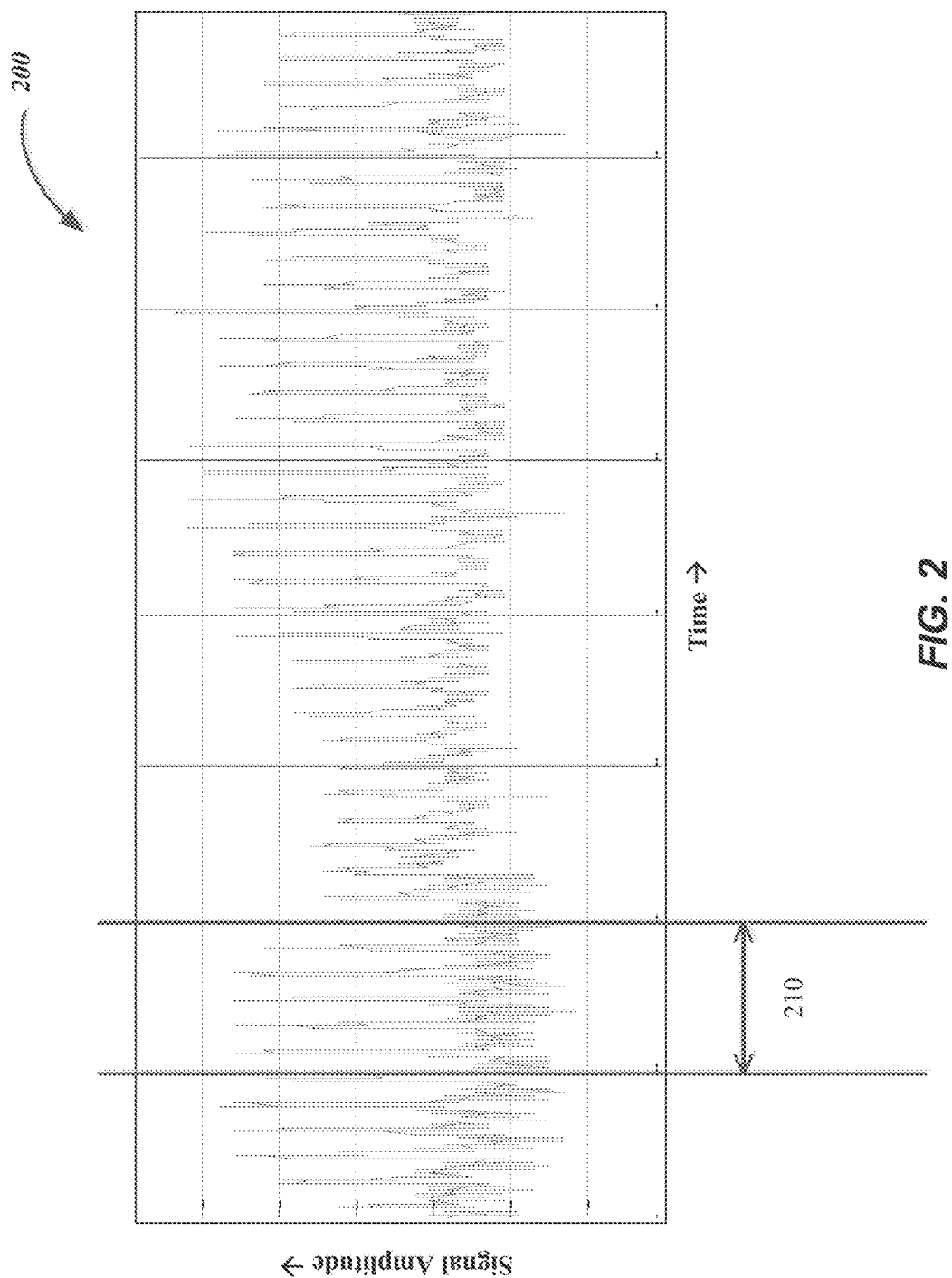
FIG. 2 illustrates an example PG signal as a function of time.

FIG. 2 is an example of an obtained PG signal as a function of time. According to implementations, the PG signal 200 can be obtained by a mobile device and used in heart rate estimation. PG signal 200 could represent light as received by a sensor in wearable device 120. One or more time epochs 210 can be extracted from PG signal 200. Two time epochs can overlap, for example, two 10 second time epochs, which are offset by one second, overlap over 9 seconds. Each time epoch extracted from the PG signal can be processed as a block or unit. For example, two or more time epochs can be sequentially extracted from the obtained PG signal by advancing successive time epoch's start time repeatedly by 1 second.

A frequency-domain PG can then be computed from the PG signal for each time epoch. For example, a Fast Fourier Transform (FFT), or other Fourier Transform, or other frequency-domain transform, can be performed on the PG signal for each time epoch. In a visual representation of the mapping using a frequency-domain plot, a signal intensity (such as amplitude or power of the signal or coefficient of the FFT) can be expressed as a function of the various frequencies present in the signal.

Figure 3:
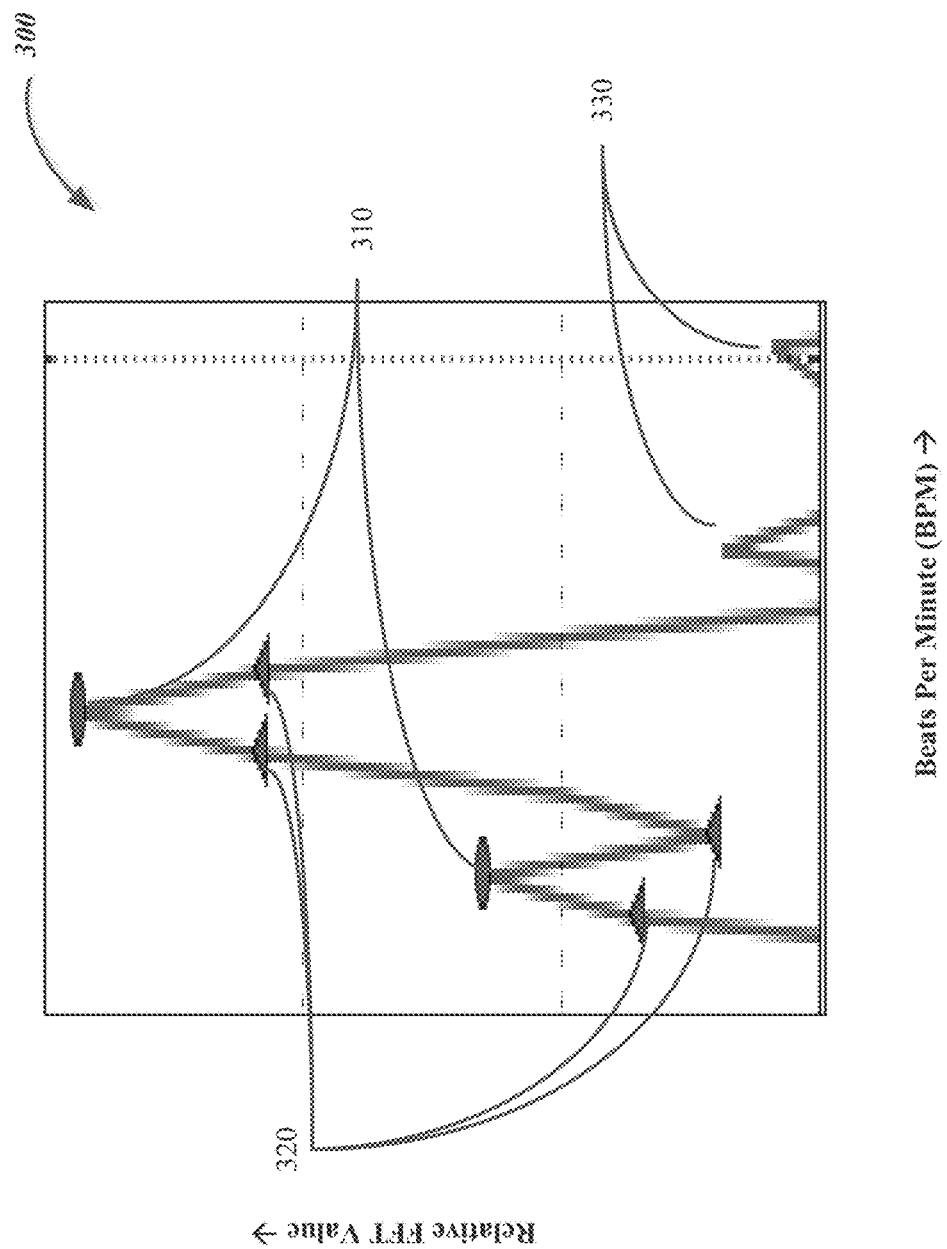
FIG. 3 illustrates an example of identifying qualified peaks from a set of peaks in a time epoch, according to an implementation.

FIG. 3 illustrates an example of identifying one or more features from the frequency-domain PG. In the example shown in FIG. 3, one or more qualified peaks are identified. In other examples, other features such as qualified troughs or valleys, widths, local maxima, thresholds, and the like can be identified. FIG. 3 illustrates plot 300 where the Y-axis represents a relative FFT value (indicative of signal intensity) and the X-axis is the frequency expressed in BPM. The peaks 310 in plot 300, indicated by ellipses, have been identified as qualified peaks; peaks 330 on the other hand have not been identified as qualified peaks.

As shown in FIG. 3, various criteria can be applied to plot 300, to identify peaks, and to further identify qualified peaks. A peak in plot 300 can represent a local maximum in the frequency domain. In plot 300, the peaks are peaks 310 and 330. Points 320, represented by triangles, are points at which the relative amplitude has fallen by a certain percentage, in the example, by more than half.

Several criteria or selection tests can be used alone or in combination for identifying qualified peaks from the peaks. For example, to be a qualified peak, the ratio of the peak's amplitude to the maximum amplitude of the power spectrum could have to exceed a certain threshold. This test may filter out low amplitude frequencies that are likely noise. To be a qualified peak, the peak's half-power bandwidth may have to be lesser than a threshold. In other words, peaks that are very wide can be filtered out. To be a qualified peak, the peak's frequency could have to lie in a certain interval. For example, to be a qualified peak, the peak could have to be in the range of 40 to 250 BPM because frequencies outside this range will likely not represent a human heart rate, at least in the situations where implementations are likely to be used.

Other criteria can be used in different implementations. In some implementations, adjacent peaks can be combined if they meet certain criteria. For example, peaks that are close together in frequencies and/or amplitudes can be combined as one peak. Although illustrated for the example of frequency-domain PG, the method explained in connection with FIG. 3 can be used to identify peaks and qualified peaks in other frequency-domain signals such as frequency-domain accelerometer signals. Accelerometer signals can be used in conjunction with PG signals for motion cancellation such as in methods described below.

Turning back to FIG. 3, peaks 310 are qualified peaks that have passed all criteria used in the implementation. On the other hand, peaks 330 have failed one or more qualification criteria, and hence have not been selected as qualified peaks. Peaks can be characterized by at least a pair of values: the amplitude (or power), and frequency. The frequency can be expressed, for example, in BPM, Hz, or an FFT bin number. Each qualified peak can be assigned a timestamp. The timestamp can represent the time of the time epoch that is being processed.

Figure 4:
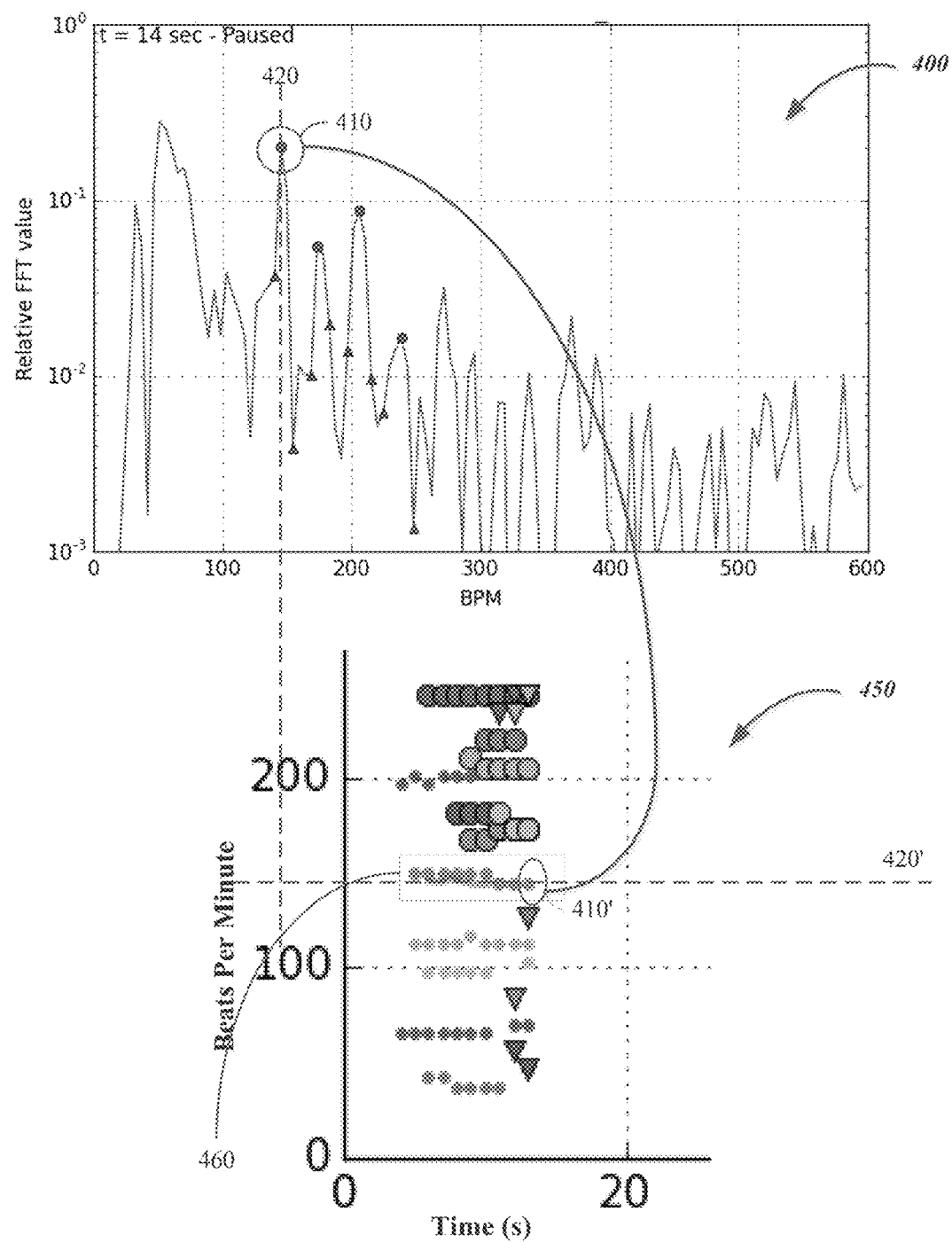
FIG. 4 illustrates an example of building traces in a frequency versus time plot from qualified peaks according to an implementation.

Qualified peaks can be used to develop a trace plot in a BPM versus time plot. The trace plot is one example of a frequency-versus-time mapping that helps visually illustrate the relationship. FIG. 4 is an illustration of an example of using a frequency domain PG 400 to develop a trace plot 450 at time epoch t=14 s. In frequency domain PG 400, qualified peaks have been identified using circles and other plot symbols. Peak 410 is an example of a qualified peak which passes all criteria of qualification. Every plot symbol (e.g. triangles, squares, circles) in trace plot 450, hereafter referred to as a 'position' represents a qualified peak, and a set of qualified peaks is added every time epoch. Although represented as a 'point' or a position in visual representations, conceptually a point in FIG. 4 refers to a frequency-time pair corresponding to a peak. As shown in FIG. 4, trace plot 450 at t=14 s includes qualified peaks for all successive time epochs from t=1 s to t=14 s.

The corresponding point to peak 410 in trace plot 450 is point 410'. The frequency associated with peak 410 is line 420 expressed in BPM. Line 420' represents the same frequency in trace plot 450. Although not expressed in trace plot 450, point 410' also has an associated relative FFT value, which is the Y-axis value in plot 400. A relative FFT value can be obtained, for example, by dividing the FFT amplitude by the maximum FFT amplitude encountered in the frequency-domain PG for all time epochs.

In trace plot 450, as data from new time epochs are obtained, positions are grouped together to build or construct "traces." Traces are constructed by identifying positions that may be representative of closely related peaks over time. For example, a peak that appears at approximately the same frequency over different time epochs may have the same cause and could form a trace in trace plot 450. In trace plot 450, one example of such a trace is the trace 460.

In trace plot 450, several criteria can be used to decide which trace or traces to which a position must belong, or whether to begin a new trace. In other words, several criteria can be used to determine if a position is related to other positions earlier in time. Each trace can capture one possible past history of a position (representative of a qualified peak) at that time. Although each trace can contain at most one position for each time epoch, a given position can belong to more than one trace for each time epoch, representing more than one possible history of that position. Traces can contain gaps in time. Thus, for each time value in trace plot 450, a given trace can contain either no or one position.

In one implementation, to develop trace plot 450 from plot 400, qualified peaks are processed in order of descending Relative FFT value. A position corresponding to a qualified peak is added to any trace whose most recent frequency differs from the qualified peak's frequency by less than a maximum frequency difference $D_{MAX}$. If a peak is not closer to any active trace than $D_{MAX}$, the qualified peak can become a position in a new active trace.

At any given time a set of active traces can be maintained. The set of active traces can be updated when a data for a new time epoch is received. When time advances by one unit, the previous set of traces can be pruned by (a) Removing from the set of active traces any trace whose trace age is older than a specified maximum age $A_{MAX}$; and/or (b) Removing short traces whose recent history coincides with that of a much longer trace. Long traces can continue to be maintained. The trace age can be the difference between a current timestamp and a previous timestamp in a trace.

Figure 5:
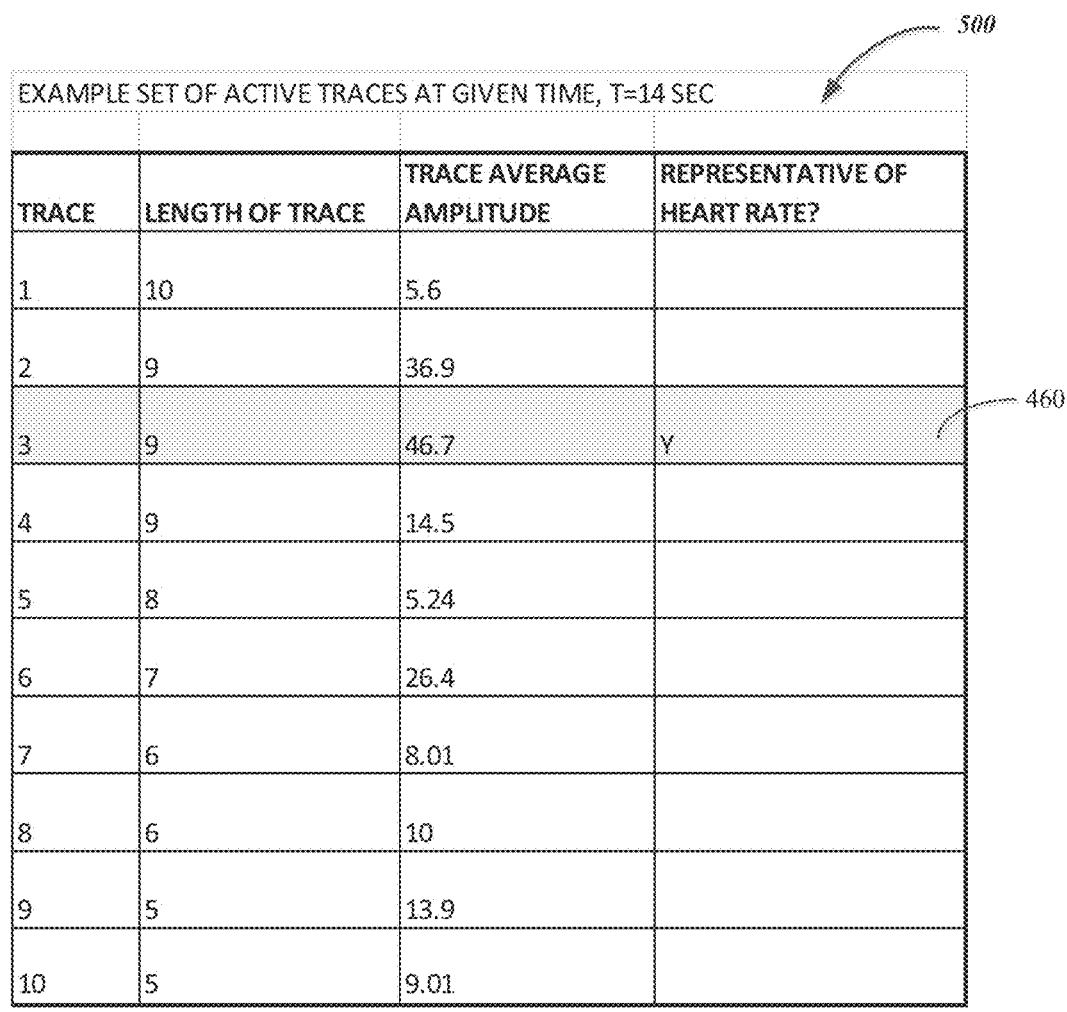
FIG. 5 illustrates an example of a set of active traces at a given time, according to an implementation.

FIG. 5 includes a table 500, which is an example set of active traces maintained at a given time, t=14 s in the example. In the example, ten active traces are maintained, including information relating to the length of each trace, the trace average amplitude of each trace, and which trace, if any, has been selected as representative of the heart rate. The trace average amplitude can represent the average amplitude of a number N of most recent peaks of a trace. N can represent a threshold value that can be adjusted based on the conditions. The trace average amplitude can be computed in several ways, such as a through a moving window average or by using a digital lowpass filter. In table 500, the trace average amplitude is indicated in arbitrary units.

In the example shown in table 500, trace 3, corresponding to trace 460 from FIG. 4 has been selected as representative of the heart rate. The selection of a trace as representative of the heart rate can be done based on several criteria. For example, very short traces along the time axis can be discarded. Two or more traces that appear to merge with time can be combined with each other. Traces can be allowed to have small gaps in time. Construction of a trace can resume after a small time gap. However, if the gap is very large, construction of a new trace can begin.

The remaining pruned set of traces can be ranked according to various criteria, for example, their length or their average amplitude, and the highest ranking trace can be selected as representative of the heart rate. In other implementations, a trace can be selected from the list of pruned traces as representative of the heart rate based on several criteria. For example, traces with higher average trace amplitude can be preferred; longer traces can be preferred over shorter traces; and traces with fewer or no time gaps can be preferred over traces with longer gaps. The other traces could be discarded as noise, harmonics, or motion artefacts.

In particular, in some examples, the set of traces can be pruned by: (a) Excluding any traces with fewer than $L_{MIN}$ time units (provided that the algorithm has been running for greater than $L_{MIN}$ time units); (b) Keeping a certain number of traces with the largest trace average amplitudes. The trace average amplitude values can be weighted more heavily for recent samples, for example, by a Finite Impulse Response (FIR) or Infinite Impulse Response (IIR) filter. The remaining traces can be scored by a trained classifier that can take into account such features as trace length (in time units), statistics of the peak amplitude time series in the trace, number of time gaps in the trace, number of other traces, and so on. The classifier can be trained using machine learning techniques. The raw heart rate can be reported based on the frequency of the final peak in the trace with the highest classifier score. In some embodiments, the raw heart rate can further be smoothed and filtered before it is reported. In some situations, all active traces could be eliminated in the pruning process, leaving no trace as representative of the heart rate. In such a scenario, a conclusion that the heart rate is unknown can be reached.

Figure 6:
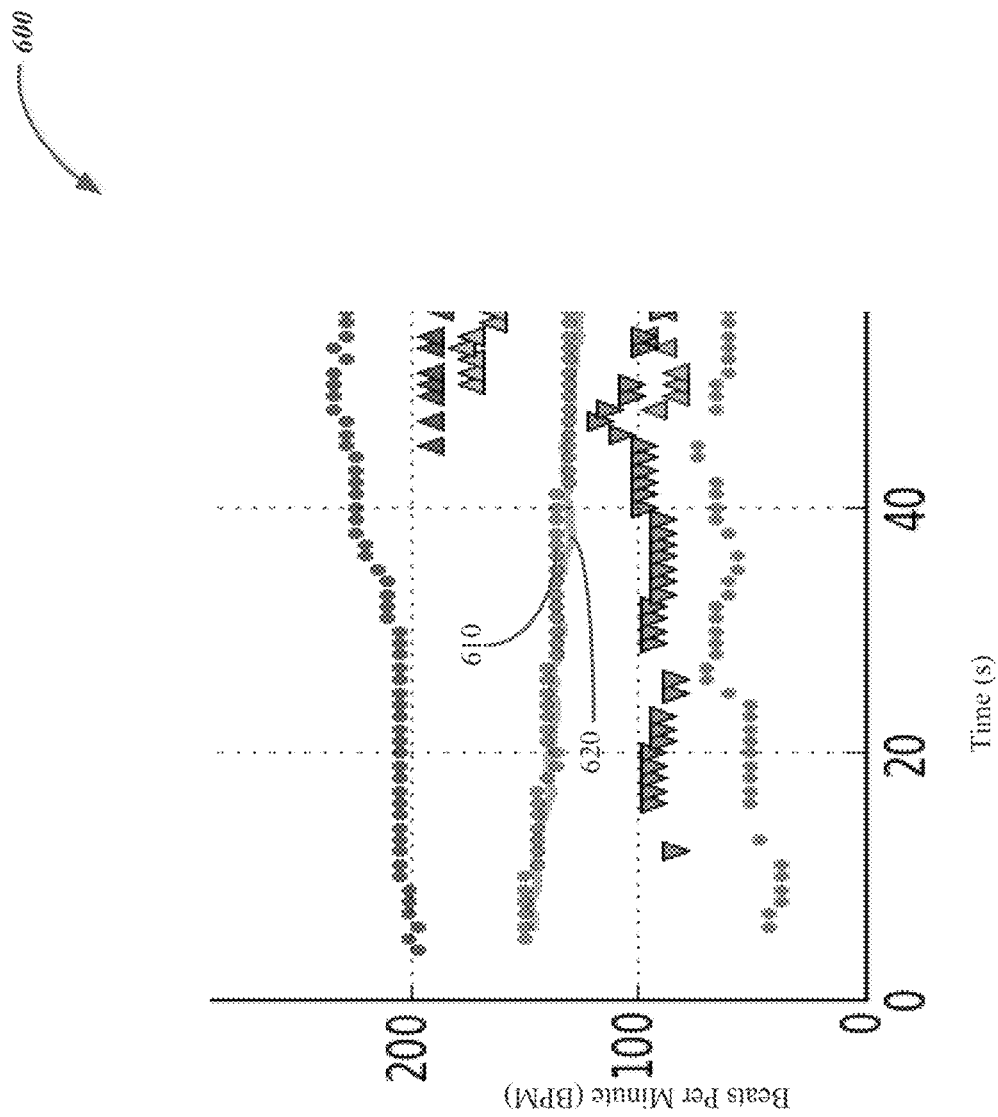
FIG. 6 is an example of heart rate estimation over time using traces according to an implementation, superimposed is a measured heart rate using a chest strap.

FIG. 6 is an example trace plot 600 over time according to an implementation. Trace plot 600 shows an example of traces computer for a PG signal, and has been built in accordance with methods described above. At the time epoch shown in FIG. 6, trace 610 has been selected as representative of the heart rate. The line 620 represents the true heart rate as measured by a consumer-grade chest-strap strapped around the user's chest. From trace plot 600, it is apparent that the trace 610 tracks the actual heart rate quite accurately.

In some implementations, artifacts from motion can be distinguished from signals from the user's heart rate through motion cancellation. In these implementations, trace processing can be performed independently for the PG signal and an accelerometer (ACL) signal. Motion cancellation can be based on the general principle that an accelerometer situated close to or mechanically coupled to the PG sensor or a device which comprises the PG sensor can measure the PG sensor's movement.

In such implementations, each trace can be expressed as a vector of ordered triples of time, frequency, and amplitude for each position in the trace. For example, time of each position can be expressed in seconds, the frequency in BPM, and the amplitude in relative (dimensionless) units. Using each admissible pair of ACL and PG traces (vectors), inter-trace distance can be computed, for example, as the root mean squared, mean absolute, or other metric of the distance. Such an inter-trace distance can be computed from the trace's ordered triples over the subset of times that are included in both the ACL and PG traces. If the inter-trace distance between an ACL trace and a PG trace is less than a threshold minimum distance $D_{MIN}$, then PG trace can be discarded as a "motion artifact". The surviving PG traces can be used for estimating the heart rate.

In implementations, to avoid excessive computation, the number of accelerometer magnitude traces compared to the PG traces can be limited by retaining only a subset of the ACL traces with average amplitudes greater than a threshold. Similarly, the maximum trace history retained can be limited to a most recent segment of positions.

In some implementations, a quality metric can be provided along with or in conjunction with a heart rate estimate. The quality metric can provide an indication of the reliability and/or accuracy of the reported heart rate. In implementations, this quality metric can be calculated based on properties of the traces used in estimating the heart rate using methods such as the methods described above. The quality metric can be used, for example, to determine whether the heart rate estimate should be displayed to the user. If the quality metric indicates that the heart rate estimate is not reliable, such a heart rate may not be displayed or otherwise provided to the user.

In some implementations, the quality metric may linearly or nonlinearly combine several components obtained from a trace plot and information related to the PG signal. For example, the quality metric can incorporate one or more of: a measure of the harmonic relations of the surviving traces at the time epoch of the heart rate estimate; a global measure of 'smoothness' of the trace selected as representative of the heart rate (for example estimated by looking at second differences, total variation, or number of zero crossings of differences); a trace length; and an average signal intensity (such as power) in the trace selected as representative of the heart rate.

Figure 7:
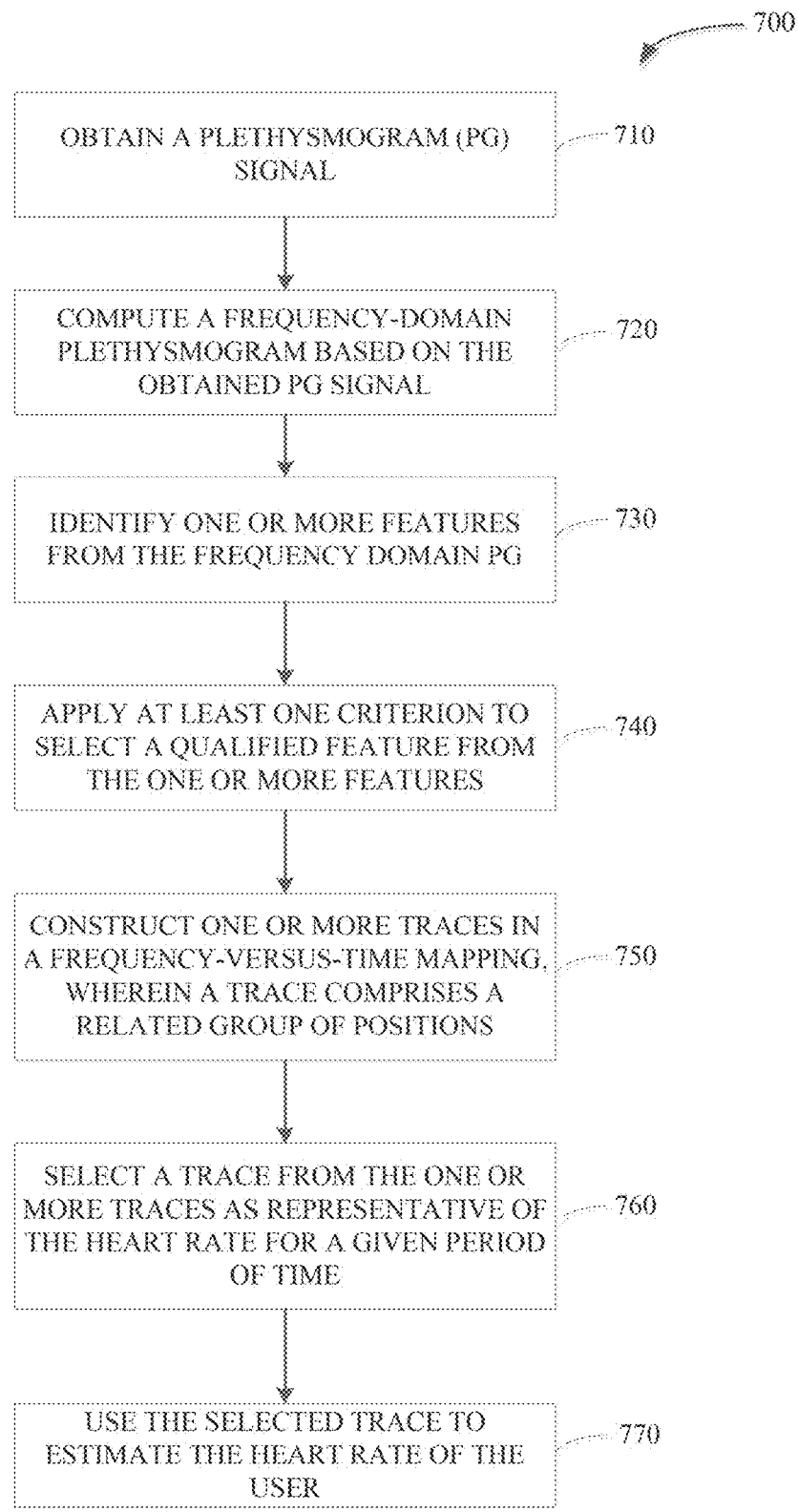
FIG. 7 illustrates an exemplary process for estimating a user's heart rate according to an implementation.

FIG. 7 illustrates an exemplary process 700 for estimating a user's heart rate according to an implementation. At block 710, process 700 includes obtaining a plethysmogram (PG) signal. In one example, the PG signal can be a photoplethysmogram (PPG), although other examples of PG signals can include inductance plethysmography, and the like. In the case of PPG, a light signal can be generated by an LED in or proximate to the sensor, and can be scattered or partially reflected from a user's skin or subcutaneous tissue or other body parts. The scattered light can be obtained by a PG sensor. The PG sensor can be comprised of, for example, a photodiode that can detect light.

At block 720, process 700 includes computing a frequency-domain plethysmogram (PG) based on the obtained PG signal. Several methods can be used to convert the PG signal to a frequency domain, such as Fourier Transform, Fast Fourier Transform (FFT), wavelet transform, and the like. In the frequency-domain PG, a signal intensity of the PG signal (such as power, amplitude, FFT coefficient) can be expressed as a function of frequency. The computation can be performed by one or more processors located in a device. In implementations, the processors can be part of a heart rate engine located in the device.

At block 730, process 700 includes identifying one or more features from the frequency-domain PG. In implementations, peaks or peak regions can be identified from the frequency-domain PG. In such implementations, various criteria can be used to identify peaks. For example, a peak can represent a local maximum of signal amplitude. The one or more features can be identified using one or more processors in a device. In some implementations, the processors can be part of the heart rate engine located in the device.

At block 740, process 700 includes applying at least one criterion to select a qualified feature from the one or more features. In implementations, application of the criteria and selection of qualified features can be performed by a peak selector engine located in the heart rate engine. Examples of criteria that can be used to select qualified features such as qualified peaks have been explained above.

At block 750, process 700 includes constructing one or more traces in a frequency versus time mapping, wherein a trace comprises a group of related positions. In implementations, positions can represent features. Examples of constructing a frequency versus time plot was described above with reference to trace plots. In implementations, constructing a trace can include adding a qualified feature to any trace whose most recent frequency differs from the qualified feature's frequency by less than a threshold difference; and constructing a new trace if the qualified feature's frequency is different from the most recent frequency of the trace by more than a threshold amount. In implementations, the frequency versus time mapping can be constructed by a trace builder engine located in the heart rate engine.

At block 760, process 700 includes selecting a trace from the one or more traces in the frequency versus time mapping as representative of the heart rate for a given period of time. A list of active traces can be maintained at the given time. The process of selecting a trace from the list of active traces can involve pruning the list based on several criteria. Examples of such criteria have been explained above. In implementations, process 800 of FIG. 8 can be used to eliminate zero or more traces. In implementations, the selection of a trace as representative of the heart rate can be performed by a trace selector engine located in the heart rate engine.

At block 770, process 700 includes using the selected trace to estimate the heart rate of the user. In some implementations not depicted in FIG. 7, no trace may be selected as indicative of the heart rate. In such implementations, process 700 can include communicating the information that the heart rate of the user could not be estimated. In implementations, process 700 can include maintaining a set of active traces, wherein maintaining the set of active traces comprises removing from the set of active traces any trace whose trace age is older than a maximum age.

Figure 8:
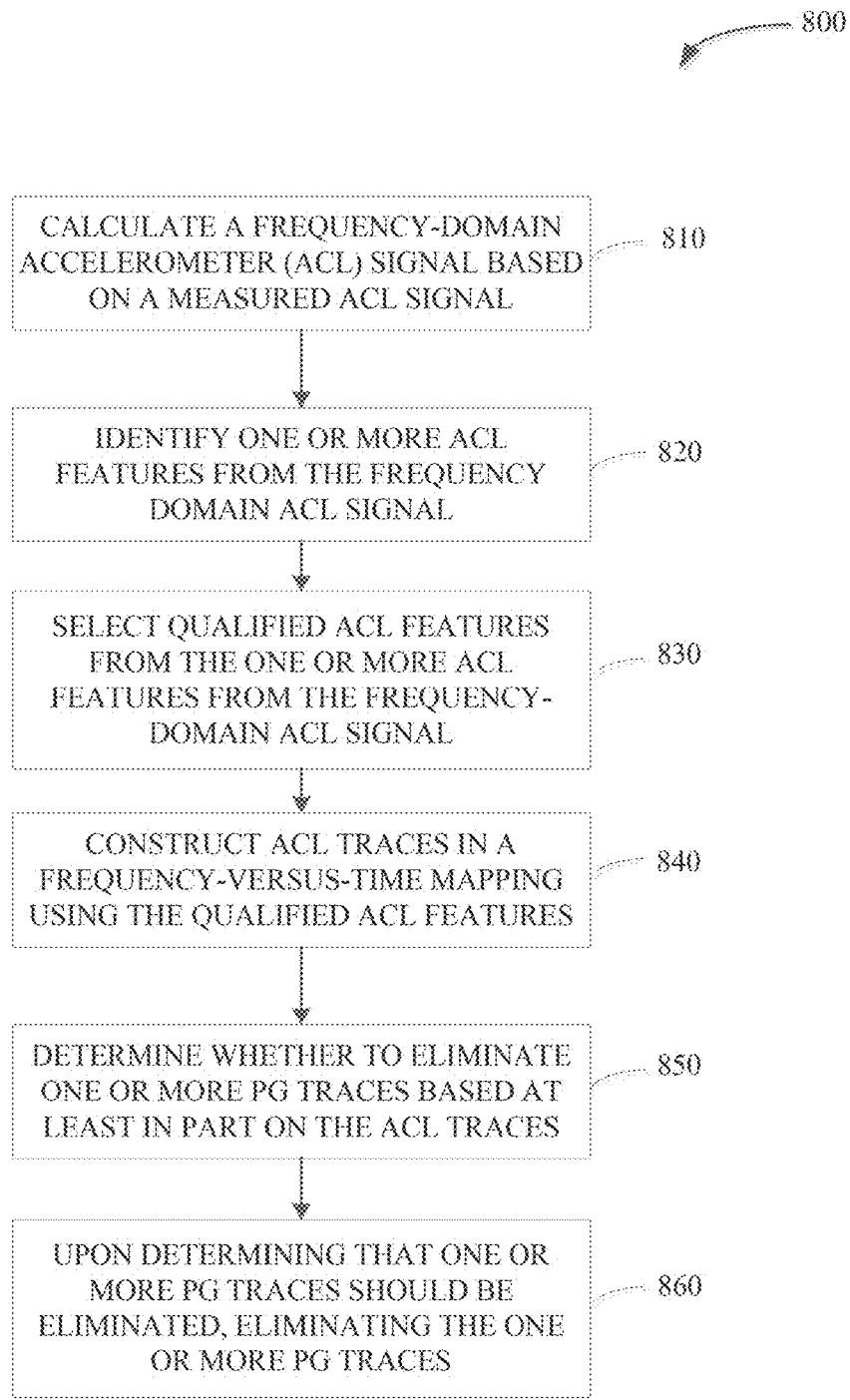
FIG. 8 illustrates an exemplary process for motion cancellation that can be used in conjunction with estimating a user's heart rate according to an implementation.

FIG. 8 illustrates an exemplary process 800 for eliminating one or more PG traces based on motion cancellation in estimating a user's heart rate according to another implementation. In implementations, process 800 can be used in conjunction with process 700, for example at block 760, to determine whether to eliminate traces. At block 810, process 800 includes calculating a frequency-domain accelerometer (ACL) signal based on an obtained ACL signal. In implementations, an ACL can be located in proximity to the PG sensor and mounted so that there is no relative motion between the ACL sensor and the PG sensor. The ACL is affected by, and substantially measures, movement that causes noise in the PG signal. Such ACL readings can be used to identify motion artefacts in the frequency versus time mapping, and cancel them.

At block 820, process 800 includes identifying one or more ACL features from the frequency-domain ACL signal. In some implementations, the features can be peaks in the frequency-domain ACL. At block 830, process 800 includes selecting qualified ACL features from the one or more ACL features from the frequency-domain ACL signal. The selection can be based on one or more criteria similar to the criteria discussed with reference to the frequency-domain PG above. At block 840, process 800 can include constructing ACL traces in the frequency versus time mapping using the qualified ACL features, each qualified ACL feature representing an ACL position in the frequency-versus-time mapping, wherein an ACL trace comprises a group of related ACL positions. In some implementations, such ACL traces can be constructed in the same plot as the PG traces; in other implementations, a separate ACL trace plot can be constructed.

At block 850, process 800 can include determining whether to eliminate one or more PG traces based at least in part on the ACL traces. Such a determination can be made, for example, by using ACL and PG trace vectors as described above. At block 860, process 800 includes, upon determining that one or more PG traces should be eliminated, eliminating the one or more PG traces. One or more steps in process 800 can be carried out by components of the heart rate engine.

In some implementations, one or more enhancements or features can be added to methods described above. For example, because periodic signals like heart rate have spectral peaks at a fundamental frequency and its integral multiples, trace selection can be augmented by examining the harmonic relations between candidate traces and for the final heart rate estimate, and selecting the one that corresponds to the fundamental heart rate frequency.

Besides, heart rate estimation can be customized for different kinds of heart rate requests, either from a user or from a device. For example, in in 'one-time' heart rate request, the heart rate can be reported only when the quality factor exceeds a stringent threshold. This is because, in a one-time request, a user is likely interested in an accurate estimate of his or her heart rate. On the other hand, when a user requests continuous monitoring of heart rate, for example during exercise, more priority can be placed on the availability of estimates through time, rather than one any single measurement of heart rate.

In some implementations, an "auto-switch" mechanism can be used. Under the auto switch mechanism, constraints on the quality of the heart rate can start off being stringent. For example, constraints on quality can be high for the first estimate of the heart rate, such that the first estimate of the heart rate is highly accurate. Subsequently, constraints on the quality can be loosened, so that the availability of the heart rate for continuous monitoring is high. In some implementations, the initial accurately estimated heart rate can be used as a guide for subsequent heart rate measurements.

In implementations, additional information or prior known information, or otherwise known information, referred herein as "prior information" can be used to improve the heart rate estimate. Under certain conditions, such as low signal conditions or high noise conditions, the heart rate can be difficult to distinguish from other sources of noise. In these situations, prior information can be used to augment or improve the heart rate estimate. Prior information can also include knowledge gathered before an estimate of the heart rate is made that can be used to improve the estimate.

For example, prior information can include general information such as the probability that resting heart rate for a given section of the population will be in a certain range. The probability can be computed for various sections such as healthy people, and based on age, gender, and other demographic information. Prior information can also include information specific to a particular user that may have been measured or estimated previously. For example, for a user of a wearable device, prior information can indicate that the resting baseline heart rate of the user is in a range near 80 BPM.

Other examples of prior information can include: known probabilities of resting heart rate for a section or sections of population; known probabilities of the correlation between movement and heart rate for a population (such as through pairs of accelerometer readings and corresponding heart rates); estimated probabilities of a user's heart rate based on previously saved good quality pairs of accelerometer readings and heart rates during previous heart rate estimation—both at rest and during activity; estimated probabilities of a user's heart rate after a period of activity based on a dynamic model for heart rate versus activity built by saved good quality 'triples' (accelerometer reading, heart rate, and time of activity); estimated probability of a user's heart rate during the recent past, estimated by recursively computing mean or median heart rates, optionally weighted by quality. Other methods and sensors can be used for estimating activity instead of or in conjunction with accelerometer reading during the capture of prior information.

Prior information can be used in various ways. In one implementation, if a quality estimate shows low confidence in the current heart rate estimate, the heart rate can be modified (by adjusting or blending or other means) using prior information. For example, when the estimated heart rate varies unrealistically (which may occur when there is high noise), the estimated heart rate can be increased or decreased to bring the estimate within expected values based on prior information. The amount of blending with prior information can depend on the quality of the estimated heart rate. For example, more smoothing may be applied during low quality portions of the estimation process, and less smoothing applied during high quality portions of the estimation. In other implementations, the estimated heart rate can be constrained within boundaries that are set based on prior information. For example, the heart rate can be constrained to be the current heart rate estimate to be above a user's resting heart rate, or a user's expected heart rate based on an activity, as determined by previous estimates of combinations of accelerometer readings and heart rates.

Figure 9:
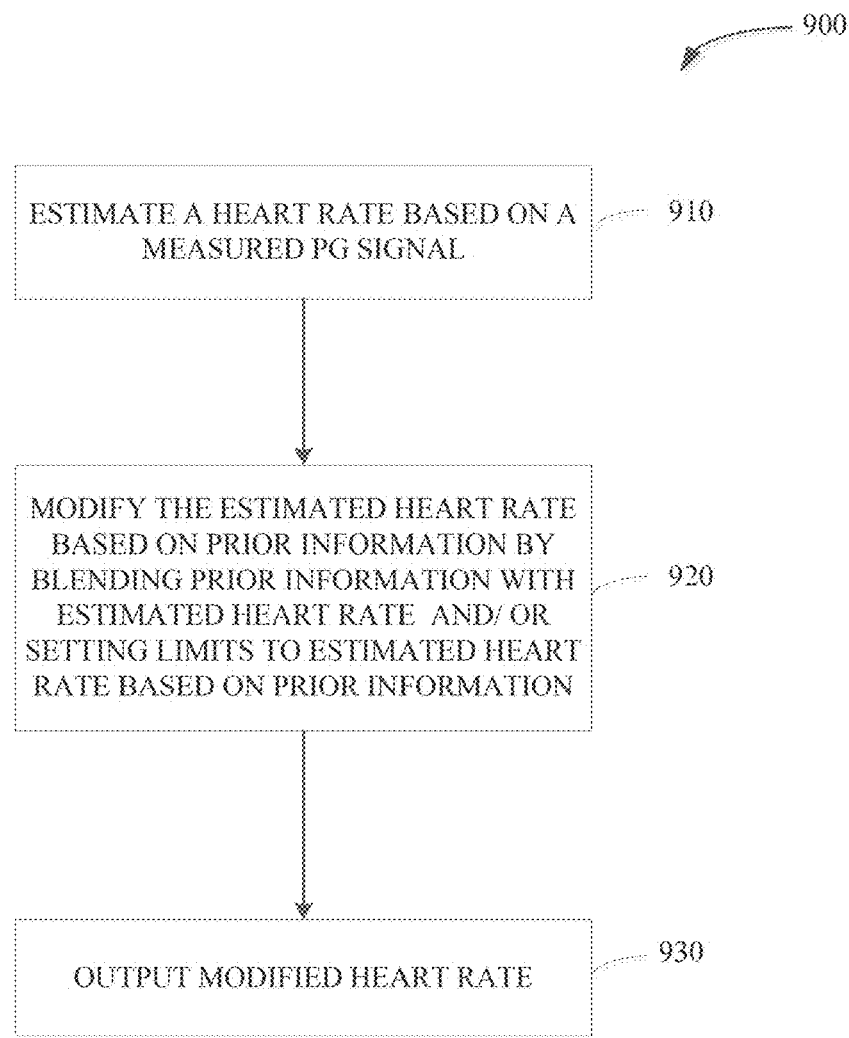
FIG. 9 illustrates an exemplary process for modifying a heart rate estimate based on prior information, according to an implementation.

FIG. 9 illustrates an exemplary process 900 for modifying a heart rate estimate based on prior information, according to an implementation. At block 910, process 900 includes estimating a heart rate based on a measured PG signal, for example by using process 700. At block 920, process 900 includes modifying the estimated heart rate based on prior information. The modification of the estimated heart rate can include blending prior information with the estimated heart rate, setting limits to the heart rate based on prior information, or a combination of the two. At block 930, process 900 includes outputting the modified heart rate. In implementations, process 900 can be performed by an intelligent estimator engine in the heart rate engine on a device.

In implementations where a user makes a one-time request for a heart rate, for example after heavy exercise, the heart rate estimate may not be available until various measurements and computations are completed. Such a request can be made by user input into a wearable device, such as by pressing a button, or activating a feature in an application on the wearable device. In some instances, the heart rate estimate may be available only after several seconds from the request time. The estimate itself may be determined as reliable to report only several seconds after the request, and the reported heart rate may refer to the heart rate several seconds following the request. However, by this time, the heart rate can change, sometimes drastically. For example, just after exercise, the reported heart rate may not be the heart rate at the time of request, since the heart rate recovers during the intervening time.

In some implementations, the heart rate can be projected backwards in time to the time at which the one-time request was made. For example, in implementations where the methods described above are used, i.e. when traces are used to estimate heart rate, backward projection can involve backtracking through the heart rate trace to the requested time. When other methods of estimating heart rate are used, a fit to a history of prior heart rate estimates can be used to extract the trend backwards in time. In implementations, two outputs of heart rate could be provided: one estimate of heart rate at the time of output, and one estimate of heart rate referring to the time of request. A heart rate estimate at the time of first request is a single value reported after the initial request.

Figure 10:
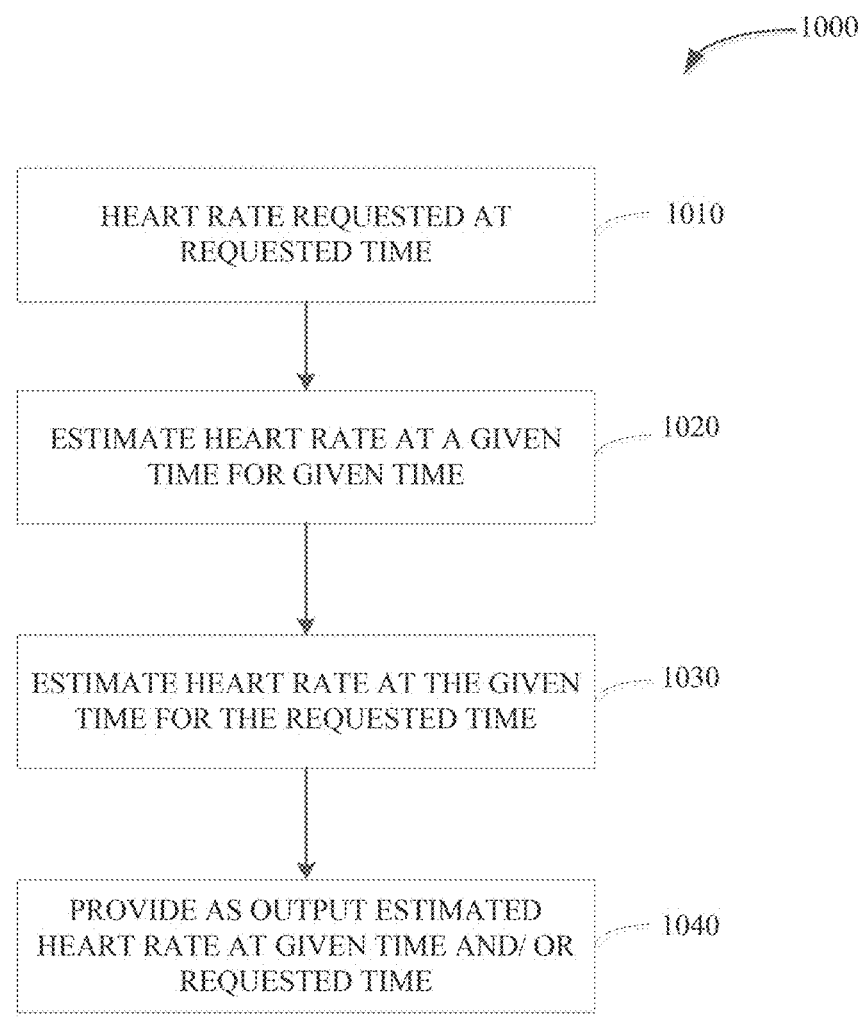
FIG. 10 illustrates an exemplary process for estimating a heart rate at a given time for a requested time, according to an implementation.

FIG. 10 illustrates an exemplary process 1000 for estimating a heart rate at a given time for a requested time, according to an implementation. At block 1010, process 1000 includes receiving a heart rate request. At block 1020, process 1000 includes estimating the heart rate at a given time for the given time. In other words, the heart rate can correspond to the heart rate at the given time. At block 1030, process 1000 includes estimating the heart rate for the requested time, at the given time. This can involve backward projection of the heart rate to the requested time. At block 1040, process 1000 includes providing as output estimated heart rates corresponding to the given time, requested time, or both.

Figure 11:
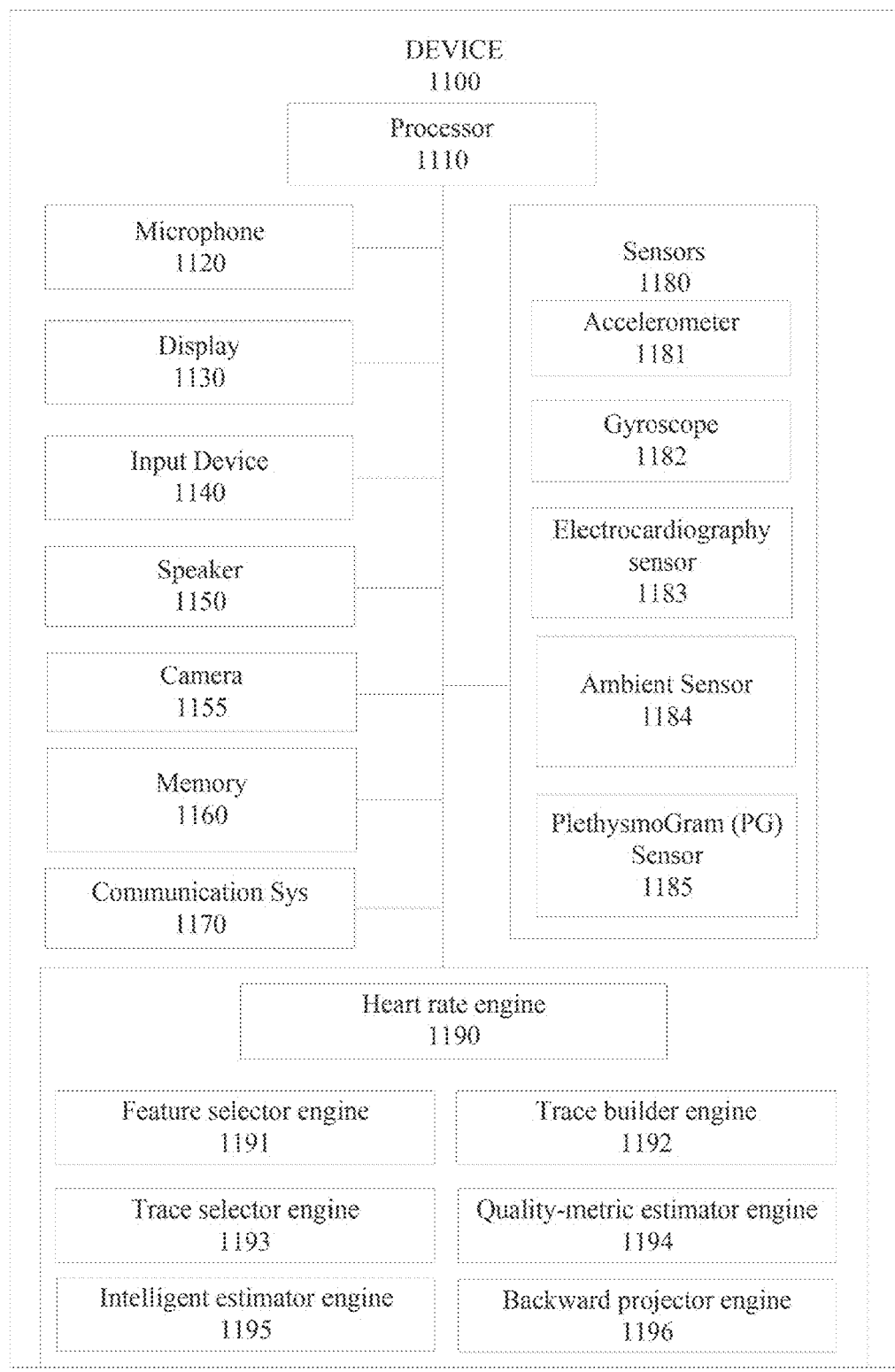
FIG. 11 shows an example device according to an implementation.

FIG. 11 shows an example computer system or device 1100 according to an implementation. An example of a computer system or device includes a desktop computer, laptop computer, tablet computer, personal data assistant, smartphone, wearable heart rate estimator or monitor, and/or any other type of special-purpose machine configured for performing calculations.

As shown in FIG. 11, device 1100 includes one or more hardware elements. The hardware elements can include a processing unit with one or more processors 1110, including without limitation one or more general-purpose processors and/or one or more special-purpose processors (such as digital signal processing chips, graphics acceleration processors, and/or the like); one or more input devices 1140, which may include without limitation a microphone 1120 remote control, a mouse, a keyboard, and/or the like; and one or more output devices, which may include without limitation a display 1130, a speaker 1150, or other output devices not shown (such as a presentation device, a printer, and/or the like).

Device 1100 may further include (and/or be in communication with) a non-transitory memory 1160, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such a memory can be configured to implement any appropriate data stores, including without limitation, various file systems, database structures, and/or the like.

Device 1100 can also include a communications system 1170, which may include without limitation a modem, a network card (wireless and/or wired), an infrared communication device, a wireless communication device and/or a chipset such as a Bluetooth device, 402.11 device, WiFi device, WiMax device, cellular communication facilities such as GSM (Global System for Mobile Communications), W-CDMA (Wideband Code Division Multiple Access), LTE (Long Term Evolution), etc., and/or the like. The communications system 1170 may permit data to be exchanged with a network (such as the network described below, to name one example), other computer systems, and/or any other devices described herein. In many examples, device 1100 can further comprise a working memory, which may include a random access memory and/or a read-only memory device, as described above.

Device 1100 also can comprise software elements, located within a working memory, including an operating system, device drivers, executable libraries, and/or other code, such as one or more application programs, which may comprise computer programs provided by various examples, and/or may be designed to implement methods, and/or configure systems, provided by other examples, as described herein. By way of example, one or more procedures described with respect to the method(s) discussed above, and/or system components can be implemented as code and/or instructions executable by a computer (and/or a processor within a computer); in an aspect, then, such code and/or instructions can be used to configure and/or adapt a general purpose computer (or other device) to perform one or more operations in accordance with the described methods.

As shown in FIG. 11, device 1100 includes sensor suite 1180. Sensor suite 1180 can comprise an accelerometer 1181 operating in accordance with principles of the present disclosure. Accelerometer 1181 can be located in physical proximity to other sensors in sensor suite 1180, and mounted in a rigid relationship to the PG sensor, including a PG sensor 1185. In one example, PG sensor 1185 can comprise a PG sensor such as pulse oximeter. In implementations, PG sensor 1185 can comprise one or more sources of light such as LEDs and one or more detectors of light such as a photodetector. PG sensor 1185 can be configured to receive PG signals. Sensor suite 1180 can include other sensors including, but not limited to gyroscope 1182, electrocardiography sensor 1183, and ambient sensor 1184.

As shown in FIG. 11, device 1100 includes a heart rate engine 1190. Heart rate engine 1190 can include one or more processors and instructions stored in a non-transitory computer readable storage medium. Heart rate engine 1190 can include a feature selector engine 1191, configured to select qualified features from a frequency domain PG signal, such as a PG signal captured by PG sensor 1185. Heart rate engine 1190 can further include a trace builder engine 1192, configured to build frequency versus time plots, or trace plots, in accordance with the present disclosure. Heart rate engine 1190 can also include a trace selector engine 1193, configured to select a trace as representative of the heart rate.

In the implementation depicted, heart rate engine 1190 can also include a quality-metric estimator engine 1194, an intelligent estimator engine 1195 that can be configured to store and use prior information in estimating the heart rate, and backward projector engine 1196. Other implementations may not include one or more of the above engines.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method of estimating heart rate of a user comprising:
obtaining a plethysmogram (PG) signal;
computing a frequency-domain PG based on the obtained PG signal, wherein the frequency-domain PG is an amplitude-versus-frequency representation of the PG signal;
identifying a plurality of features from the frequency-domain PG, wherein the plurality of features are peaks or troughs;
applying a set of criteria to identify a subset of the plurality of features as being qualified features, wherein the set of criteria are applied to the frequency-domain PG and include an amplitude based threshold and a bandwidth based threshold, and wherein applying the set of criteria comprises selecting, as qualified features, those features that meet the amplitude based threshold and the bandwidth based threshold;
after identifying the qualified features, constructing a plurality of traces in a frequency-versus-time mapping using the qualified features, each qualified feature representing a position in the frequency-versus-time mapping, wherein each trace comprises a group of related positions, and wherein the constructing of the plurality of traces comprises, for each qualified feature:
adding the qualified feature to any trace whose most recent frequency differs from the qualified feature's frequency by less than a threshold frequency difference; and
starting a new trace using the qualified feature when there are no existing traces for which the most recent frequency differs from the qualified feature's frequency by less than the threshold frequency difference;
wherein each trace is started as a new trace using a single qualified feature, and wherein at least one of the traces includes an additional qualified feature added based on a most recent frequency of the trace differing from a frequency of the additional qualified feature by less than the threshold frequency difference;
selecting a trace from the plurality of traces as representative of the heart rate for a given period of time; and
using the selected trace to estimate the heart rate of the user.

2. The method of claim 1, wherein each of the plurality of features corresponds to a peak.

3. The method of claim 1, further comprising:
calculating a frequency-domain accelerometer (ACL) signal based on an obtained ACL signal;
identifying a plurality of ACL features from the frequency-domain ACL signal;
selecting qualified ACL features from the plurality of ACL features from the frequency-domain ACL signal;
constructing ACL traces in the frequency-versus-time mapping using the qualified ACL features, each qualified ACL feature representing an ACL position in the frequency-versus-time mapping, wherein an ACL trace comprises a group of related ACL positions;
determining whether to eliminate one or more PG traces based at least in part on the ACL traces; and
upon determining that one or more PG traces should be eliminated, eliminating the one or more PG traces.

4. The method of claim 1, further comprising:
maintaining a set of active traces, wherein maintaining the set of active traces comprises removing from the plurality of traces any trace whose trace age is older than a maximum age.

5. The method of claim 1, further comprising estimating a quality metric for the heart rate.

6. The method of claim 1, further comprising modifying the estimated heart rate based on prior information.

7. The method of claim 6, wherein the prior information comprises known probabilities of pairs of accelerometer power and heart rate for a specific demographic of population.

8. The method of claim 1, wherein the heart rate is estimated at a given time for a requested time, wherein the requested time is earlier than the given time.

9. The method of claim 3, wherein the determining whether to eliminate one or more PG traces comprises:
eliminating PG traces if an inter-trace distance between an ACL trace and a PG trace is lesser than a threshold distance.

10. The method of claim 8, wherein estimating the heart rate for a requested time comprises back-tracking through a heart rate trace to the requested time.

11. The method of claim 1, wherein the frequency-domain PG is computed by applying a Fourier Transform to the PG signal, the amplitudes of the frequency-domain PG corresponding to Fourier Transform values, and wherein the plurality of traces are constructed by processing the qualified features in an order determined based on the Fourier Transform values.

12. The method of claim 1, wherein the frequency-domain PG comprises a power spectrum of the PG signal, wherein the qualified features are peaks, and wherein each qualified feature is a peak for which the ratio of the peak's amplitude to a maximum amplitude of the power spectrum of the PG signal exceeds the amplitude based threshold.

13. The method of claim 12, wherein each qualified feature is a peak for which the peak's half-power bandwidth is less than the bandwidth based threshold.

14. The method of claim 1, wherein selecting the trace from the plurality of traces comprises:
ranking the plurality of traces based on at least one of length or average amplitude, wherein a highest ranking trace is selected as representative of the heart rate.

15. A mobile device comprising:
a sensor configured to generate a plethysmogram (PG) signal based on a condition of a user; and
a processor configured to:

compute a frequency domain PG signal based on the generated PG signal, wherein the frequency-domain PG is an amplitude-versus-frequency representation of the PG signal;

identify a plurality of features from the frequency-domain PG signal, wherein the plurality of features are peaks or troughs;

apply a set of criteria to identify a subset of the plurality of features as being qualified features, wherein the set of criteria are applied to the frequency-domain PG and include an amplitude based threshold and a bandwidth based threshold, and wherein applying the set of criteria comprises selecting, as qualified features, those features that meet the amplitude based threshold and the bandwidth based threshold;

after identifying the qualified features, construct a plurality of traces in a frequency-versus-time mapping using the qualified features, each qualified feature representing a position in the frequency-versus-time mapping, wherein each trace comprises a group of related positions, and wherein the constructing of the plurality of traces comprises, for each qualified feature:

adding the qualified feature to any trace whose most recent frequency differs from the qualified feature's frequency by less than a threshold frequency difference; and starting a new trace using the qualified feature when there are no existing traces for which the most recent frequency differs from the qualified feature's frequency by less than the threshold frequency difference;

wherein each trace is started as a new trace using a single qualified feature, and wherein at least one of the traces includes an additional qualified feature added based on a most recent frequency of the trace differing from a frequency of the additional qualified feature by less than the threshold frequency difference;

select a trace from the plurality of traces as representative of the heart rate for a given period of time; and use the selected trace to estimate the heart rate of the user.

16. The mobile device of claim 15, wherein each of the plurality of features corresponds to a peak.

17. The mobile device of claim 15 wherein the computing the frequency-domain PG signal based on the generated PG signal comprises applying a Fast Fourier Transform to the generated PG signal.

18. The mobile device of claim 15, further comprising:
an accelerometer configured to generate an accelerometer (ACL) signal based on a motion of the user;
wherein the processor is further configured to:
calculate a frequency-domain ACL signal based on the generated ACL signal;
identify a plurality of ACL features from the frequency-domain ACL signal;
select qualified ACL features from the plurality of ACL features from the frequency-domain ACL signal;
construct ACL traces in the frequency versus time mapping using the qualified ACL features, each qualified ACL feature representing an ACL position in the frequency-versus-time mapping, wherein an ACL trace comprises a group of related ACL positions;
determine whether to eliminate one or more PG traces based at least in part on the ACL traces; and
upon determining that one or more PG traces should be eliminated, eliminate the one or more PG traces.

19. The mobile device of claim 15, wherein the processor is further configured to maintain a set of active traces, wherein maintaining the set of active traces comprises removing from the plurality of traces any trace whose trace age is older than a maximum age.

20. The mobile device of claim 15, wherein the processor is further configured to estimate a quality metric for the heart rate.

21. The mobile device of claim 15, wherein the processor is further configured to modify the estimate heart rate based on prior information, and wherein the prior information comprises known probabilities of pairs of accelerometer power and heart rate for a specific demographic of population.

22. The mobile device of claim 15, wherein the processor is further configured to estimate the heart rate at a given time for a requested time, wherein the requested time is earlier than the given time.

23. The mobile device of claim 18, wherein the determining whether to eliminate one or more PG traces comprises:
eliminating PG traces if an inter-trace distance between an ACL trace and a PG trace is lesser than a threshold distance.

24. An apparatus comprising:
means to generate a plethysmogram (PG) signal based on a condition of a user; and
processing means comprising:
means to compute a frequency domain PG signal based on the generated PG signal, wherein the frequency-domain PG is an amplitude-versus-frequency representation of the PG signal;
means to identify a plurality of features from the frequency-domain PG signal, wherein the plurality of features are peaks or troughs;
means to apply a set of criteria to identify a subset of the plurality of features as being qualified features, wherein the set of criteria are applied to the frequency-domain PG and include an amplitude based threshold and a bandwidth based threshold, and wherein applying the set of criteria comprises selecting, as qualified features, those features that meet the amplitude based threshold and the bandwidth based threshold;
means to, after identifying the qualified features, construct a plurality of traces in a frequency-versus-time mapping using the qualified features, each qualified feature representing a position in the frequency-versus-time mapping, wherein each trace comprises a group of related positions, and wherein the constructing of the plurality of traces comprises, for each qualified feature:
adding the qualified feature to any trace whose most recent frequency differs from the qualified feature's frequency by less than a threshold frequency difference; and
starting a new trace using the qualified feature when there are no existing traces for which the most recent frequency differs from the qualified feature's frequency by less than the threshold frequency difference;
wherein each trace is started as a new trace using a single qualified feature, and wherein at least one of the traces includes an additional qualified feature added based on a most recent frequency of the trace differing from a frequency of the additional qualified feature by less than the threshold frequency difference;

means to select a trace from the plurality of traces as representative of the heart rate for a given period of time; and means to use the selected trace to estimate the heart rate of the user.

25. The apparatus of claim 24, further comprising:

means to generate an accelerometer (ACL) signal based on a motion of the user;

wherein the processing means further comprises:

means to calculate a frequency-domain ACL signal based on the generated ACL signal;

means to identify a plurality of ACL features from the frequency-domain ACL signal;

means to select qualified ACL features from the plurality of ACL features from the frequency-domain ACL signal;

means to construct ACL traces in the frequency versus time mapping using the qualified ACL features, each qualified ACL feature representing an ACL position in the frequency-versus-time mapping, wherein an ACL trace comprises a group of related ACL positions;

means to determine whether to eliminate one or more PG traces based at least in part on the ACL traces; and upon determining that one or more PG traces should be eliminated, means to eliminate the one or more PG traces.

26. The apparatus of claim 24, wherein the processing means further comprises means to modify the estimate heart rate based on prior information.

27. The apparatus of claim 24, wherein the processing means further comprises means to estimate the heart rate at a given time for a requested time, wherein the requested time is earlier than the given time.

28. A non-transitory computer-readable medium having stored instructions thereon, which when executed by a processor, perform a method comprising:

obtaining a plethysmogram (PG) signal;

computing a frequency-domain PG based on the obtained PG signal, wherein the frequency-domain PG is an amplitude-versus-frequency representation of the PG signal;

identifying a plurality of features from the frequency-domain PG, wherein the plurality of features are peaks or troughs;

applying a set of criteria to identify a subset of the plurality of features as being qualified features, wherein the set of criteria are applied to the frequency-domain PG and include an amplitude based threshold and a bandwidth based threshold, and wherein applying the set of criteria comprises selecting, as qualified features, those features that meet the amplitude based threshold and the bandwidth based threshold;

after identifying the qualified features, constructing a plurality of traces in a frequency-versus-time mapping using the qualified features, each qualified feature representing a position in the frequency-versus-time mapping, wherein each trace comprises a group of related positions, and wherein the constructing of the plurality of traces comprises, for each qualified feature:

adding the qualified feature to any trace whose most recent frequency differs from the qualified feature's frequency by less than a threshold frequency difference; and starting a new trace using the qualified feature when there are no existing traces for which the most recent frequency differs from the qualified feature's frequency by less than the threshold frequency difference;

wherein each trace is started as a new trace using a single qualified feature, and wherein at least one of the traces includes an additional qualified feature added based on a most recent frequency of the trace differing from a frequency of the additional qualified feature by less than the threshold frequency difference;

selecting a trace from the plurality of traces as representative of the heart rate for a given period of time; and using the selected trace to estimate the heart rate of the user.

* * * * *